(12) United States Patent
Tani (10) Patent No.: US 11,653,974 B2
(45) Date of Patent: May 23, 2023

(54) TISSUE JOINER (71) Applicant: Micron Shiga Inc., Shiga (JP)

(72) Inventor: Tohru Tani, Shiga (JP)

(73) Assignee: MICRON SHIGA INC., Shiga (JP)

(*) Notice: Subject to any disclaimer, the term of this patent is extended or adjusted under 35 U.S.C. 154(b) by 651 days.

(21) Appl. No.: 16/336,476

(22) PCT Filed: Sep. 28, 2017

(86) PCT No.: PCT/JP2017/035163
§ 371 (c)(1),
(2) Date: Mar. 26, 2019

(87) PCT Pub. No.: WO2018/062369
PCT Pub. Date: Apr. 5, 2018

(65) Prior Publication Data
US 2020/0069369 A1    Mar. 5, 2020

(30) Foreign Application Priority Data
Sep. 29, 2016 (JP) .............................. JP2016-192177

(51) Int. Cl.
*A61B 18/18* (2006.01)
*A61B 18/00* (2006.01)

(52) U.S. Cl.
CPC ............. *A61B 18/1815* (2013.01); *A61B 2018/00589* (2013.01); *A61B 2018/00982* (2013.01); *A61B 2018/1861* (2013.01)

(58) Field of Classification Search
CPC ... A61B 18/18; A61B 18/1815; A61B 18/085; A61B 18/1442; A61B 18/1445; A61B 18/1447; A61B 2018/1838; A61B 2018/00589; A61B 2018/00982; A61B 2018/1861; A61B 2018/00196; A61B 2018/0063; A61B 2018/00619; A61B 2018/00595; A61B 2018/00607; A61B 17/1608; A61B 2017/2926;
(Continued)

(56) References Cited

U.S. PATENT DOCUMENTS 6,224,593 B1 * 5/2001 Ryan .................. A61B 18/1815
606/49
6,267,761 B1 * 7/2001 Ryan .................. A61B 18/1442
606/41
(Continued)

FOREIGN PATENT DOCUMENTS

JP       2013031669 A       2/2013

OTHER PUBLICATIONS

International Search Report and Written Opinion issued in corresponding International Patent Application No. PCT/JP2017/035163 (with English translation of International Search Report) dated Dec. 19, 2017 (10 pages).

*Primary Examiner* — Thomas A Giuliani
(74) *Attorney, Agent, or Firm* — Kilyk & Bowersox, P.L.L.C.

(57) ABSTRACT

Developed is a tissue joining device for endoscopic surgery, which can be used in NOTES, or the like. As a result of intensive studies carried out to solve the problem described above, the inventors of the present invention have conceived of two tissue joining device having quite novel structures and completed the present invention.

6 Claims, 7 Drawing Sheets

(58) Field of Classification Search
CPC .... A61B 2017/2933; A61B 2017/2944; A61B 2017/2948
USPC ................ 606/33, 40, 41, 48–52, 205, 207; 607/101, 154–156
See application file for complete search history.

(56) References Cited

U.S. PATENT DOCUMENTS

| | | | |
|---|---|---|---|
| 2004/0068274 A1* | 4/2004 | Hooven | A61B 18/1442 606/151 |
| 2005/0203499 A1 | 9/2005 | Pendekanti et al. | |
| 2007/0054539 A1* | 3/2007 | Wakikaido | A61B 18/1442 439/402 |
| 2010/0249769 A1* | 9/2010 | Nau, Jr. | A61B 18/18 606/33 |
| 2013/0282002 A1 | 10/2013 | Tani et al. | |
| 2014/0194865 A1 | 7/2014 | Tani et al. | |
| 2015/0366605 A1 | 12/2015 | Morejohn et al. | |

* cited by examiner

TISSUE JOINER

TECHNICAL FIELD

The present invention relates to a device configured to bring tissue pieces together by coagulating and fastening tissues with use of microwaves instead of suturing with use of a suture thread, thereby attaining substantially the same effect as suturing for the targeted attaching tissues, that is, to a tissue joining device (stitch), particularly to a tissue joining device for surgery with a narrow view, and more particularly to a tissue joining device for endoscopic surgery.

This application is a National Stage Application of PCT/JP2017/035163, filed Sep. 28, 2017, which claims priority from Japanese Patent Application No. 2016-192177, the disclosure of which is incorporated herein by reference.

BACKGROUND ART

There has been known natural orifice translumenal endoscopic surgery (NOTES) as minimally invasive surgery by which a wound is not made on a body surface. In the case of NOTES, it has been proposed that an endoscope be inserted, for example, via a rectum or a vagina. In the case of such surgery, it is required that cholecystectomy be performed by allowing the endoscope to proceed via a stomach, open a hole in a wall of the stomach, and then enter an abdominal cavity. Among the entire processing, a removal method for cholecystectomy has already been established, and hence a conventional method can be used. However, it is required that an operation to close the hole in the stomach be performed at the end. Furthermore, it is also required that the hole be closed at the time of perforation of the stomach. However, there is currently no endoscope suturing device which can deal with this problem.

A literature related to a suturing device using microwaves (see Patent Literature 1) has been reported. In particular, the inventors of the present invention have succeeded in producing a prototype tissue suturing device using microwaves (see Patent Literature 2).

However, the structure of a tissue joining device of the present invention is quite different from the structures of the tissue suturing devices described in those literatures.

CITATION LIST

Patent Literature

[PTL 1] JP 11-47144 A
[PTL 2] WO 2013/089257 A1

SUMMARY OF INVENTION

Technical Problem

Figure 1:
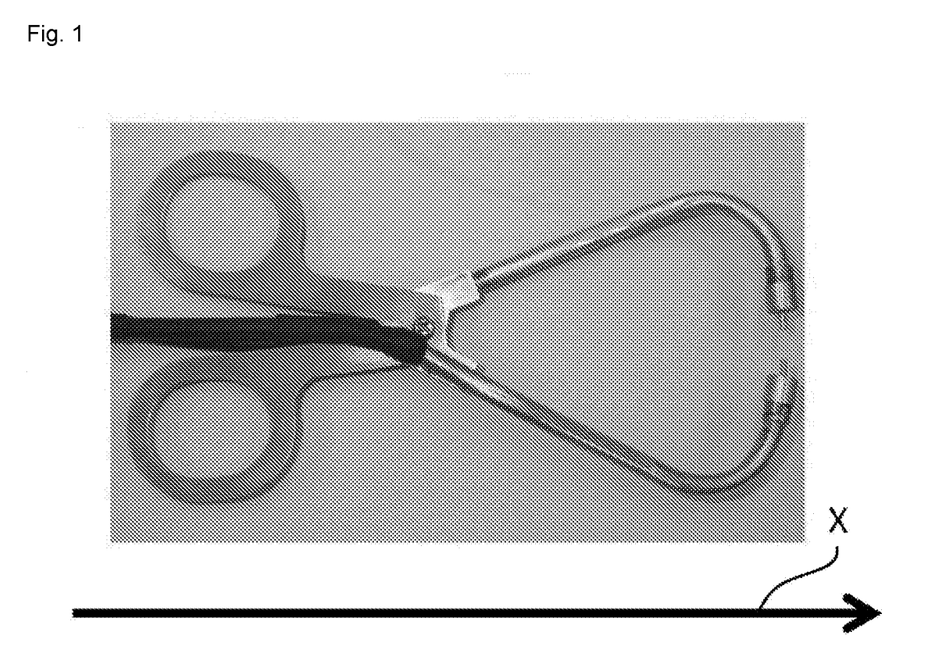
FIG. 1 is a photograph of a related-art tissue suturing device using microwaves.

In the related-art tissue suturing device using microwaves, a motion to sandwich sutured target tissue portions is performed in a direction substantially perpendicular to a longitudinal axis direction of the suturing device. Therefore, the device can be used at the time of laparotomy or the like in surgery with a wide-field, but it is difficult to use the device in a thin tube of an endoscope (see FIG. 1). Further, the motion of the related-art tissue suturing device using the microwaves to sandwich the sutured target tissue portions was also difficult to be performed in the longitudinal axis direction of the suturing device.

That is, an object of the present invention is a development of a tissue joining device for endoscopic surgery, which can be used in NOTES, or the like.

Solution to Problem

As a result of intensive studies carried out to solve the problem described above, the inventors of the present invention have conceived of two tissue joining devices having quite novel structures and completed the invention.

Tissue Joining Device including Protruding Section and Receiving Section (see FIGS. 2A to 2C to FIGS. 4A and 4B)

Provided is a tissue joining device, including: a protruding section directly or indirectly connected to a central conductor and/or an external conductor configured to apply microwaves, or a protruding section including the central conductor and/or the external conductor configured to apply microwaves; and a receiving section directly or indirectly connected to the central conductor and/or the external conductor configured to apply microwaves, or a receiving section including the central conductor and/or the external conductor configured to apply microwaves, wherein the protruding section includes a tip oriented in a distal direction of a longitudinal axis, the receiving section includes a tip oriented in a proximal direction of the longitudinal axis, and the tip of the protruding section is located on a proximal side with respect to the tip of the receiving section on the longitudinal axis, and the tip of the protruding section is configured to move in the distal direction and/or the tip of the receiving section is configured to move in the proximal direction of the longitudinal axis, or wherein the protruding section includes a tip oriented in the proximal direction of the longitudinal axis, the receiving section includes a tip oriented in the distal direction of the longitudinal axis, and the tip of the receiving section is located on a proximal side with respect to the tip of the protruding section on the longitudinal axis, and the tip of the protruding section is configured to move in the proximal direction and/or the tip of the receiving section is configured to move in the distal direction of the longitudinal axis, and wherein, through the movement of the tip of the protruding section and the tip of the receiving section, portions of targeted attaching tissues are brought into contact with each other or placed on one another by the protruding section and the receiving section, and further, the portions having been brought into contact with each other or placed on one another are coagulated and/or fastened with use of microwaves to fix the target tissues.

Tissue Joining Device including a plurality of Tissue Graspers (see FIGS. 6A to 6C and FIGS. 7A and 7B)

Provided is a tissue joining device, including: a plurality of tissue graspers directly or indirectly connected to a central conductor and/or an external conductor configured to apply microwaves and each including a tip having a shape which enables grasping tissues, or a plurality of tissue graspers each including the central conductor and/or the external conductor configured to apply microwaves and each including a tip having a shape which enables grasping tissues; and a tissue-grasper accommodating cylinder configured to accommodate the plurality of tissue graspers, wherein the plurality of tissue graspers are released when the tissue-grasper accommodating cylinder moves in a proximal direction of a longitudinal axis, further, the tips of the plurality of tissue graspers cause portions of targeted attaching tissues to be brought into contact with each other or placed on one another when the tissue-grasper accommodating cylinder moves in a distal direction of the longitudinal axis, and further, the portions having been brought into contact with each other or placed on one another are coagulated and/or fastened with use of microwaves to fix the target tissues.

That is, the present invention includes the following features.

1. A tissue joining device, including: a protruding section directly or indirectly connected to a central conductor and/or an external conductor configured to apply microwaves, or a protruding section including the central conductor and/or the external conductor configured to apply microwaves; and a receiving section directly or indirectly connected to the central conductor and/or the external conductor configured to apply microwaves, or a receiving section including the central conductor and/or the external conductor configured to apply microwaves, wherein the protruding section includes a tip oriented in a distal direction of a longitudinal axis, the receiving section includes a tip oriented in a proximal direction of the longitudinal axis, and the tip of the protruding section is located on a proximal side with respect to the tip of the receiving section on the longitudinal axis, and the tip of the protruding section is configured to move in the distal direction and/or the tip of the receiving section is configured to move in the proximal direction of the longitudinal axis, or wherein the protruding section includes a tip oriented in the proximal direction of the longitudinal axis, the receiving section includes a tip oriented in the distal direction of the longitudinal axis, and the tip of the receiving section is located on a proximal side with respect to the tip of the protruding section on the longitudinal axis, and the tip of the protruding section is configured to move in the proximal direction and/or the tip of the receiving section is configured to move in the distal direction of the longitudinal axis, and wherein, through the movement of the tip of the protruding section and the tip of the receiving section, portions of targeted attaching tissues are brought into contact with each other or placed on one another by the protruding section and the receiving section, and further, the portions having been brought into contact with each other or placed on one another are coagulated and/or fastened with use of microwaves to fix the target tissues.

2. The tissue joining device according to above-mentioned Item 1, wherein the tip of the protruding section is oriented in the proximal direction of the longitudinal axis, and the tip of the receiving section is oriented in the distal direction of the longitudinal axis.

3. The tissue joining device according to above-mentioned Item 1 or 2, wherein the tip of the protruding section is oriented in the proximal direction of the longitudinal axis, the tip of the receiving section is oriented in the distal direction of the longitudinal axis, and the tip of the protruding section is configured to move in the proximal direction of the longitudinal axis.

4. The tissue joining device according to any one of above-mentioned Items 1 to 3, wherein the tip of the protruding section is oriented in the proximal direction of the longitudinal axis, the tip of the receiving section is oriented in the distal direction of the longitudinal axis, and the tip of the protruding section is configured to move in the proximal direction of the longitudinal axis, and wherein the protruding section is directly or indirectly connected to the central conductor or the external conductor configured to apply microwaves, and the receiving section is directly or indirectly connected to the central conductor or the external conductor configured to apply microwaves.

5. The tissue joining device according to any one of above-mentioned Items 1 to 3, wherein the tip of the protruding section is oriented in the distal direction of the longitudinal axis, the tip of the receiving section is oriented in the proximal direction of the longitudinal axis, and the tip of the protruding section is configured to move in the distal direction of the longitudinal axis, and wherein the protruding section is directly or indirectly connected to the central conductor or the external conductor configured to apply microwaves, and the receiving section is directly or indirectly connected to the central conductor or the external conductor configured to apply microwaves.

6. The tissue joining device according to any one of above-mentioned Items 1 to 5, wherein the tissue joining device is to be used for surgery with a narrow view, especially for endoscopic surgery.

7. The tissue joining device according to any one of above-mentioned Items 1 to 5, wherein the tissue joining device is to be used for endoscopic surgery.

8. A tissue joining device, including: a plurality of tissue graspers directly or indirectly connected to a central conductor and/or an external conductor configured to apply microwaves and each including a tip having a shape which enables grasping tissues, or a plurality of tissue graspers each including the central conductor and/or the external conductor configured to apply microwaves and each including a tip having a shape which enables grasping tissues; and a tissue-grasper accommodating cylinder configured to accommodate the plurality of tissue graspers, wherein the plurality of tissue graspers are released when the tissue-grasper accommodating cylinder moves in a proximal direction of a longitudinal axis, further, the tips of the plurality of tissue graspers cause portions of targeted attaching tissues to be brought into contact with each other or placed on one another when the tissue-grasper accommodating cylinder moves in a distal direction of the longitudinal axis, and further, the portions having been brought into contact with each other or placed on one another are coagulated and/or fastened with use of microwaves to fix the target tissues.

9. The tissue joining device according to above-mentioned Item 8, including: two tissue graspers directly or indirectly connected to the central conductor and/or the external conductor configured to apply microwaves and each including a tip having a shape which enables grasping the tissues; and a tissue-grasper accommodating cylinder configured to accommodate the two tissue graspers, wherein the two tissue graspers are released when the tissue-grasper accommodating cylinder moves in the proximal direction of the longitudinal axis, further, the tips of the two tissue graspers cause portions of targeted attaching tissues to be brought into contact with each other or placed on one another when the tissue-grasper accommodating cylinder moves in the distal direction of the longitudinal axis, and further, the portions having been brought into contact with each other or placed on one another are coagulated and/or fastened with use of the microwaves to fix the target tissues.

Advantageous Effects of Invention

The tissue joining device including the protruding section and the receiving section and the tissue joining device including the plurality of tissue graspers can be used as a tissue joining device for surgery with a narrow view, especially for endoscopic surgery.

In detail, after removal of the protruding section and the receiving section having been pressed against tissues, the tissues are coagulated and fastened. Thus, the tissues on opposite sides are fastened by pressure and connected to each other, thereby being fixed to each other. Therefore, tissues can be joined substantially as in the case in which the tissues are sutured with a suture thread.

BRIEF DESCRIPTION OF DRAWINGS

FIGS. 2A to 2C are views for illustrating a first mode of the tissue joining device including a protruding section and a receiving section, in which

FIGS. 3A to 3C are views for illustrating a second mode of the tissue joining device including the protruding section and the receiving section, in which

FIGS. 4A and 4B are photographs of a prototype example of the tissue joining device including the protruding section and the receiving section, in which

DESCRIPTION OF EMBODIMENTS

Embodiments of the present invention are described with reference to the accompanying drawings. However, these drawings are merely examples which symbolically represent features of the present invention, and the present invention is not limited thereto.

(Tissue Joining Device Including Protruding Section and receiving section)

A tissue joining device (1) including a protruding section and a receiving section as one of the tissue joining devices of the present invention has at least the following structures.

A protruding section (2) directly or indirectly connected to a central conductor (7) and/or an external conductor (8) configured to apply microwaves, or a protruding section (2) including the central conductor (7) and/or the external conductor (8) configured to apply microwaves.

A receiving section (3) directly or indirectly connected to the central conductor (7) and/or the external conductor (8) configured to apply microwaves, or a receiving section (3) including the central conductor (7) and/or the external conductor (8) configured to apply microwaves.

(First Mode of Tissue Joining Device Including Protruding Section and Receiving Section)

Figure 2A:
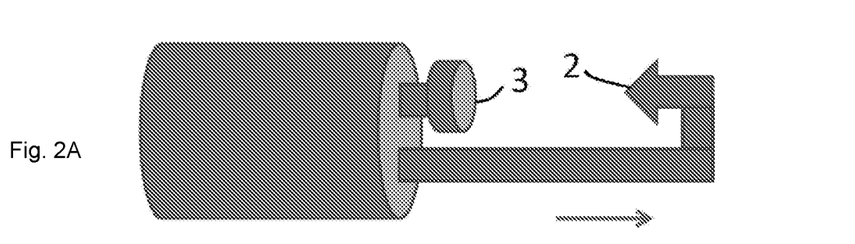
FIG. 2A is an external view of the tissue joining device including the protruding section and the receiving section.

The protruding section (2) includes a tip oriented in a proximal direction of a longitudinal axis (X) of the tissue joining device, the receiving section (3) includes a tip oriented in a distal direction of the longitudinal axis (X), and the tip of the protruding section (2) is located on a distal side with respect to the tip of the receiving section (3) on the longitudinal axis (X) (see FIG. 2A).

When the tip of the protruding section (2) moves in the proximal direction of the longitudinal axis (X) (see FIG. 2B), and/or the tip of the receiving section (3) moves in the distal direction of the longitudinal axis (X) (see FIG. 2C), portions of targeted attaching tissues are brought into contact with each other or placed on one another by the protruding section (2) and the receiving section (3). Further, the portions having been brought into contact with each other or placed on one another are coagulated and/or fastened with use of microwaves to fix the target tissues.

Fixing means a state in which the portions of the targeted attaching tissues are fixed with each other, and includes, for example, joining.

"Portions of targeted attaching tissues" means portions to be joined in the targeted attaching tissues, and includes, for example, pieces or fragments of the tissues.

The movement in the distal direction and the proximal direction of the longitudinal axis includes not only a movement substantially in parallel with the X but also a movement approximately in parallel (for example, a movement inclined by 1 degree to 40 degrees, 1 degree to 30 degrees, 1 degree to 20 degrees, 1 degree to 10 degrees, 1 degree to 8 degrees, and 1 degree to 5 degrees with respect to X).

(Second Mode of Tissue Joining Device Including Protruding Section and Receiving Section)

Figure 3A:
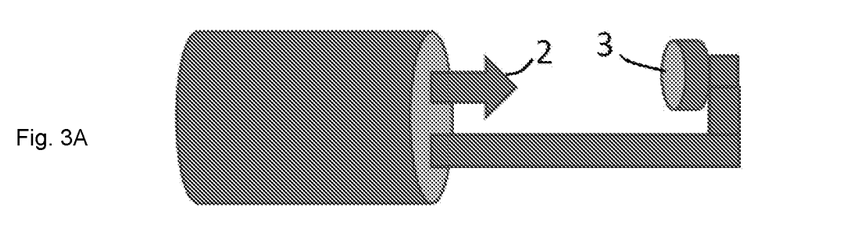
FIG. 3A is an external view of the tissue joining device including the protruding section and the receiving section.

The receiving section (3) includes a tip oriented in the proximal direction of the longitudinal axis (X) of the tissue joining device, the protruding section (2) includes a tip oriented in the distal direction of the longitudinal axis (X), and the tip of the receiving section (3) is located on a distal side with respect to the tip of the protruding section (2) on the longitudinal axis (X) (see FIG. 3A).

When the tip of the receiving section (3) moves in the proximal direction of the longitudinal axis (X) (see FIG. 3B), and/or the tip of the protruding section (2) moves in the distal direction of the longitudinal axis (see FIG. 3C), the portions of the targeted attaching tissues are brought into contact with each other or placed on one another by the protruding section (2) and the receiving section (3). Further, the portions having been brought into contact with each other or placed on one another are coagulated and/or fastened with use of microwaves to fix the target tissues.

(Protruding Section)

Figure 5A:
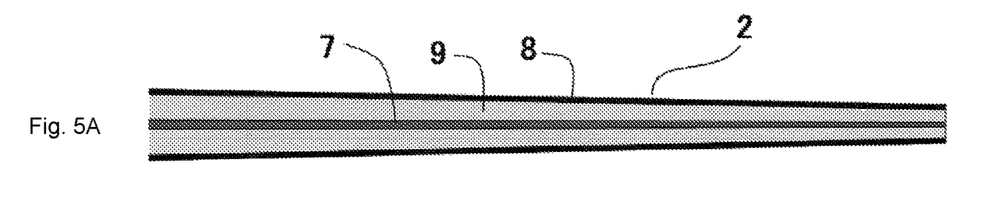
FIG. 5A is a view for illustrating the protruding section (2) having a tapered-off tip.
Figure 5B:
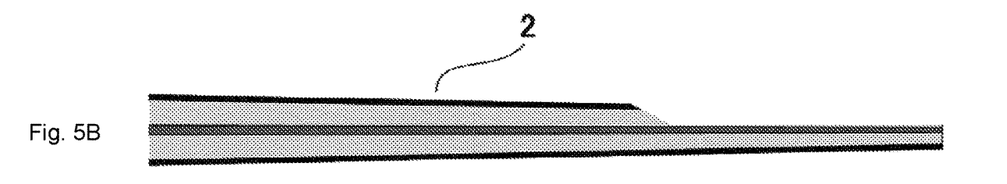
FIG. 5B is a view for illustrating the protruding section (2) having a tapered-off tip with a halved structure.
Figure 5C:
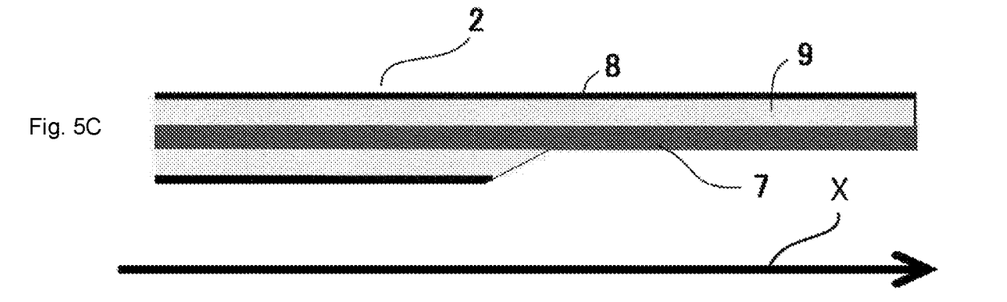
FIG. 5C is a view for illustrating the protruding section (2) having the halved structure.
Figure 6A:
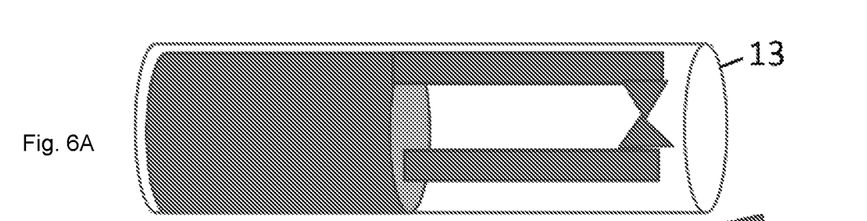
FIG. 6A is a view for illustrating a mode of the tissue joining device including a plurality of tissue graspers.
Figure 6B:
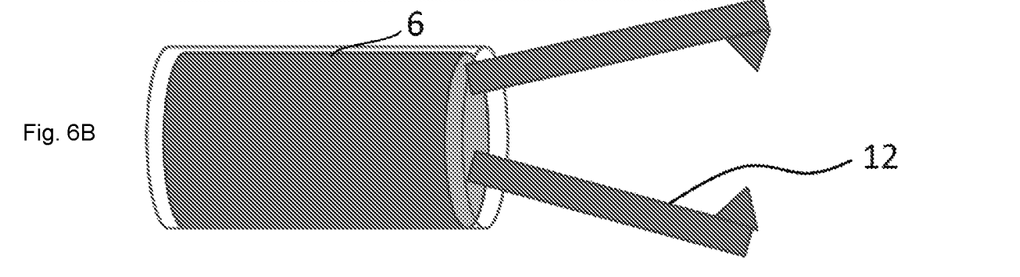
FIG. 6B is a schematic view for illustrating the plurality of graspers (12) which are freely released from a tissue-grasper accommodating cylinder (13)
Figure 6C:
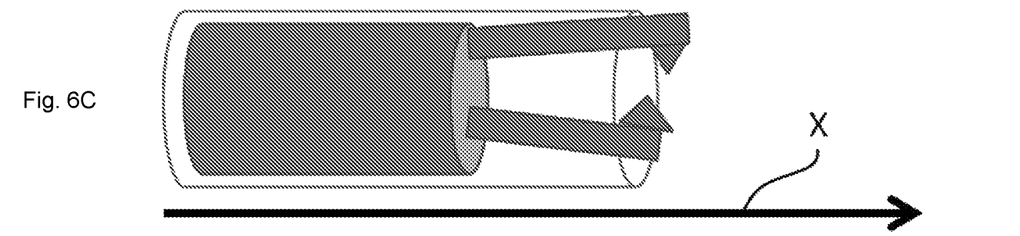
FIG. 6C is a schematic view for illustrating a state in which tips of the plurality of tissue graspers (12) cause the portions of the targeted attaching tissues to be brought into contact with each other or placed on one another (tissues are not illustrated).

A structure and a shape of the protruding section (2) are not particularly limited as long as the protruding section (2) can cause the portions of the targeted attaching tissues to be brought into contact with each other or placed on one another with use of the receiving section (3), and further can apply microwaves. However, in consideration that the targeted attaching tissues are pressed against the receiving section (3), the tip may have a tapered-off shape, a cylindrical or rectangular columnar plane, or a polygonal-prism or a non-circle cylinder (elliptical cylinder) plane. In the case of the protruding section (2) including the central conductor (7) configured to apply microwaves, the central conductor (7) is exposed from an insulator (9) at an end portion thereof (see FIGS. 5A to 5C).

It is preferred that the protruding section (2) be reduced in diameter gradually or stepwisely toward the tip. The inventors of the present invention have confirmed that such a tapered-off protruding section (2) (tapered-off structure, see FIG. 5A) can efficiently apply microwaves to targeted coagulating tissues, and further, can reduce damage to non-targeted coagulating tissues.

Further, the protruding section (2) may have a halved structure (a half of a column longitudinally cut in half about a middle portion (may be formed in an acute angle), the central conductor (7) configured to transmit microwaves is arranged at the center of the column, and the central conductor is exposed when the column is cut in half. In a forming method, a coaxial structure may be formed in which an insulating layer is arranged between the central conductor (7) and the external conductor (8), and the coaxial structure is cut longitudinally to be formed to have a halved shape in which the central conductor (7) is exposed vertically (see FIG. 5C).

The inventors of the present invention have confirmed that the protruding section (2) in such a halved structure can apply microwaves to the targeted coagulating tissues, and further, can reduce damage to the non-targeted coagulating tissues.

Figure 2B:
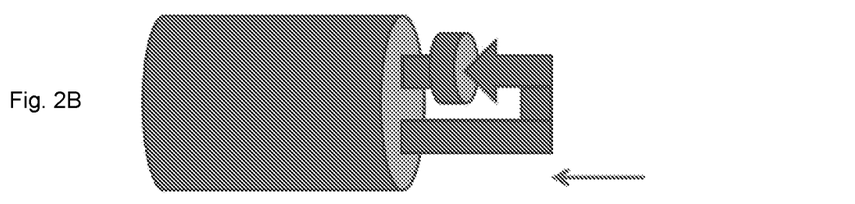
FIG. 2B is a schematic view for illustrating a state in which a tip of the protruding section (2) moves in a proximal direction of a longitudinal axis (X) to cause portions of targeted attaching tissues to be brought into contact with each other or placed on one another (tissues are not illustrated)
Figure 2C:
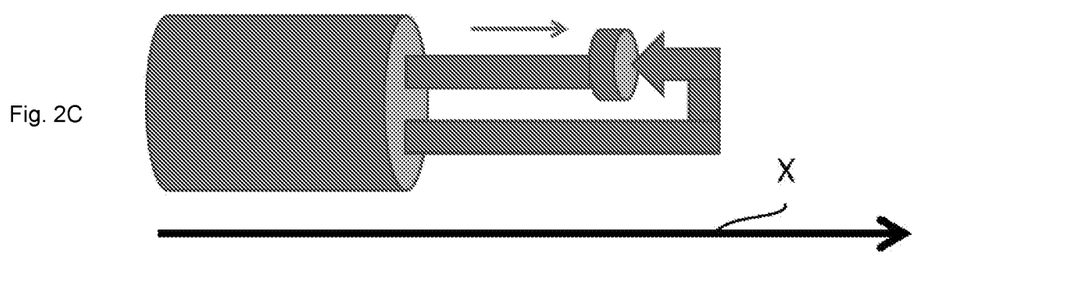
FIG. 2C is a schematic view for illustrating a state in which a tip of the receiving section (3) moves in a distal direction of the longitudinal axis to cause the portions of the targeted attaching tissues to be brought into contact with each other or placed on one another (tissues are not illustrated).
Figure 3B:
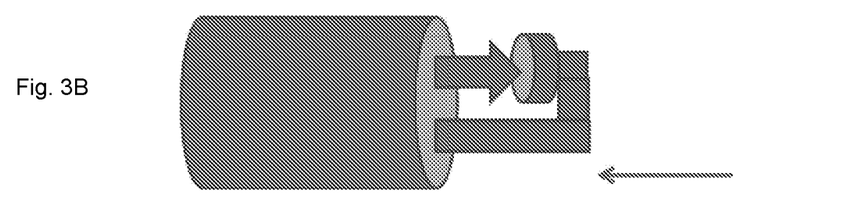
FIG. 3B is a schematic view for illustrating a state in which the tip of the receiving section (3) moves in the proximal direction of the longitudinal axis (X) to cause the portions of the targeted attaching tissues to be brought into contact with each other or placed on one another (tissues are not illustrated)
Figure 3C:
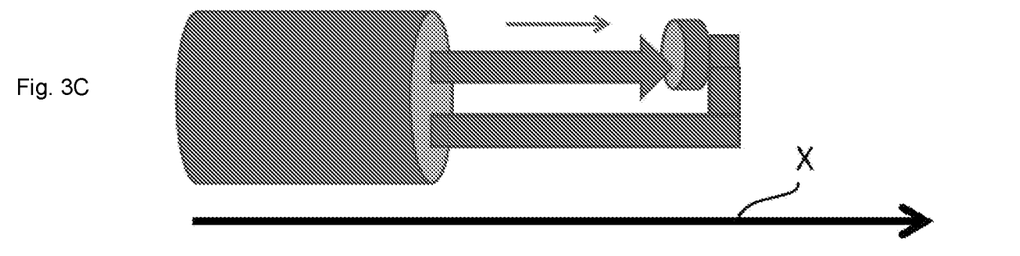
FIG. 3C is a schematic view in which the tip of the protruding section (2) moves in the distal direction of the longitudinal axis (X) to cause the portions of the targeted attaching tissues to be brought into contact with each other or placed on one another (tissues are not illustrated).

When the tip of the protruding section (2) is oriented in the proximal direction of the longitudinal axis (X) of the tissue joining device as illustrated in FIGS. 2A to 2C, the protruding section (2) has an arrow shape in numeric 7 shape (the tip has an arrowhead shape) (see FIG. 2A). When the tip is oriented in the distal direction of the longitudinal axis (X) of the tissue joining device as illustrated in FIGS. 3A to 3C, the protruding section (2) has a straight arrow shape (see FIG. 3A).

As a mechanism for moving the protruding section (2) in the proximal or distal direction of the longitudinal axis (X), a mechanism used in a conventional medical instrument can be adopted. For example, the protruding section (2) can be moved in the proximal direction of the longitudinal axis (X) by pulling an end of the protruding section (2) in the proximal direction of the longitudinal axis (X), and the protruding section (2) can be moved in the distal direction of the longitudinal axis (X) by pushing the end of the protruding section (2) in the distal direction of the longitudinal axis (X).

(Receiving Section)

A structure and a shape of the receiving section (3) is not particularly limited as long as the receiving section (3) can cause the portions of the targeted attaching tissues to be brought into contact with each other or placed on one another with the protruding section (2), and further can apply microwaves. In consideration of the receiving section for the targeted attaching tissues, the receiving section (3) may have a dish shape, a cylindrical shape, a polygonal-prism shape, a non-circle cylinder shape (elliptical cylinder shape) or the like. In the case of the receiving section (3) including the external conductor (8) configured to apply microwaves, an entirety or a part (especially a surface) of the receiving section (3) is made of an electrical conductor.

As a mechanism for moving the receiving section (3) in the proximal or distal direction of the longitudinal axis (X), a mechanism used in the conventional medical instrument can be used. For example, the receiving section (3) can be moved in the proximal direction of the longitudinal axis (X) by pulling the end of the receiving section (3) in the proximal direction of the longitudinal axis (X), and the receiving section (3) can be moved in the distal direction of the longitudinal axis (X) by pushing the end of the receiving section (3) in the distal direction of the longitudinal axis (X).

(Preferred Mode of Tissue Joining Device Including Protruding Section and Receiving Section)

Figures 4A, 4B:
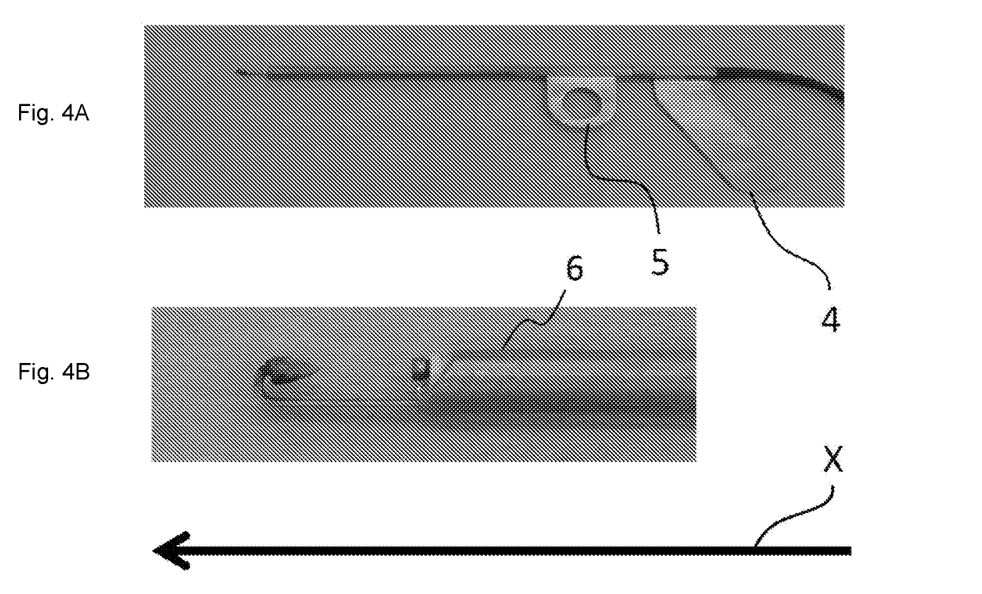
FIG. 4A is an external view of the prototype example.
FIG. 4B is an enlarged view of the tip.

A preferred mode and a preferred method of use of the tissue joining device (1) including the protruding section and the receiving section of the present invention are illustrated in FIGS. 4A and 4B, and details are as follows.

The protruding section (2) is directly or indirectly connected to the central conductor (7) configured to apply microwaves, and the receiving section (3) is directly or indirectly connected to the external conductor (8) configured to apply microwaves. The protruding section (2) may be connected to the external conductor (8), and the receiving section (3) may be connected to the central conductor (7).

The tip of the protruding section (2) is oriented in the proximal direction of the longitudinal axis (X) of the tissue joining device, the tip of the receiving section (3) is oriented in the distal direction of the longitudinal axis (X), and the tip of the protruding section (2) is located on the distal side with respect to the tip of the receiving section (3) (see FIG. 4B).

In addition, the tissue joining device (1) includes a grip (4), a trigger (5) and a holder (6). The holder (6) includes the central conductor (7) and the external conductor (8).

When a user or an operator (doctor) holds the grip (4) in the hand and moves (pulls) the trigger (5) in the proximal direction of the longitudinal axis (X) with the index finger, the tip of the protruding section (2) is moved in the proximal direction of the longitudinal axis (X). Accordingly, the portions of the targeted attaching tissues are brought into contact with each other or placed on one another by the protruding section (2) and the receiving section (3), and are coagulated and/or fastened with use of microwaves to fix (join) the target tissues.

(Application of Tissue Joining Device Including Protruding Section and Receiving Section)

In the tissue joining device (1) including the protruding section and the receiving section of the present invention, the protruding section (2) and/or the receiving section (3) move in the longitudinal axis (X) direction. Thus, unlike the related-art tissue joining device (see FIG. 1), the tissue joining device (1) can be used in a thin tube, and can be preferably used in endoscopic surgery, endoscopic surgery, catheter surgery, and the like.

(Tissue Joining Device Including a plurality of Tissue Graspers)

A tissue joining device (11) including a plurality of tissue graspers (12) each including a tip having a shape which enables grasping tissues as one of tissue joining devices of the preset invention has at least the following structures.

A plurality of tissue graspers (12) directly or indirectly connected to the central conductor (7) and/or the external conductor (8) configured to apply microwaves and each including a tip having a shape which enables grasping the tissues, or a plurality of tissue graspers (12) each including the central conductor (7) and/or the external conductor (8) configured to apply microwaves and each including a tip having a shape which enables grasping the tissues.

A tissue-grasper accommodating cylinder (13) configured to accommodate the plurality of tissue graspers.

Figure 7A:
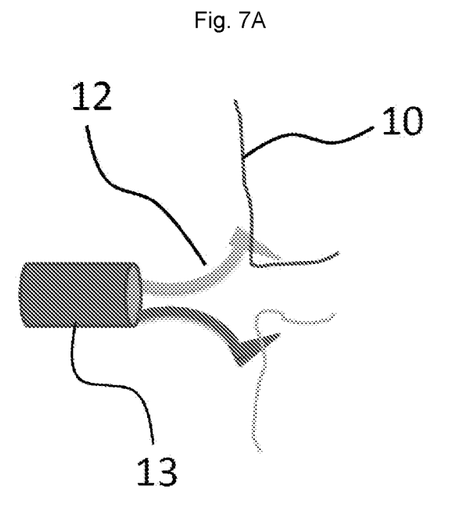
FIG. 7A is a schematic view for illustrating a state in which the two tissue graspers (12) grasp the tissues.

When the tissue-grasper accommodating cylinder (13) moves in the proximal direction of the longitudinal axis (X), the plurality of tissue graspers (12) are released (see FIG. 6B), and further grasp the tissues (see FIG. 7A). Next, when the tissue-grasper accommodating cylinder (13) moves in the distal direction of the longitudinal axis (X), the tips of the plurality of tissue graspers (12) cause the portions of the targeted attaching tissues to be brought into contact with each other or placed on one another (see FIG. 6C and FIG. 7B). Further, the portions having been brought into contact with each other or placed on one another are coagulated and/or fastened with use of microwaves to fix (join) the target tissues.

(Tissue Grasper)

The tissue grasper (12) of the present invention is not particularly limited as long as the tip can grasp the tissue. The tissue grasper (12) may have a hook shape (including a multiple hook shape), a barb shape (including a multiple barb shape), a fishhook shape (including a multiple fishhook shape), or a protruding shape. Further, it is preferred that the tissue grasper (12) be made of a material such as a shape memory alloy which returns to an original predetermined position.

A base portion except the tip of the tissue grasper (12) may be curved (see FIG. 7A). When the base portion is curved, it is preferred that the tissue grasper (12) have elasticity.

(Tissue-Grasper Accommodating Cylinder)

The tissue-grasper accommodating cylinder (13) of the present invention is not particularly limited as long as the cylinder can accommodate the plurality of tissue graspers (12). Further, when the tissue-grasper accommodating cylinder (13) moves in the proximal direction of the longitudinal axis (X), the plurality of tissue graspers (12) is released (opened) from the cylinder.

(Preferred Mode of Tissue Joining Device Including a plurality of Tissue Graspers)

Figure 7B:
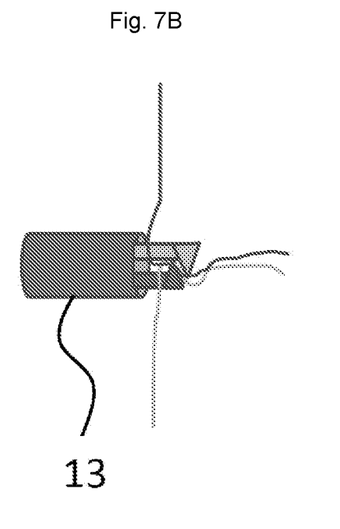
FIG. 7B is a schematic view for illustrating a state in which the tips of the two tissue graspers (12) cause the portions of the targeted attaching tissues to be brought into contact with each other or placed on one another.

A preferred mode and a preferred method of use of the tissue joining device (11) including the plurality of tissue graspers (12) of the present invention are illustrated in FIGS. 7A and 7B, and details are as follows.

Two tissue graspers (12) are provided. One tissue grasper (12) is directly or indirectly connected to the central conductor (7) configured to apply microwaves, and another tissue grasper (12) is directly or indirectly connected to the external conductor (8) configured to apply microwaves.

The tips of the two tissue graspers (12) have a hook shape. One tissue grasper (12) is shorter than another tissue grasper (12) so as to be easily accommodated in the tissue-grasper accommodating cylinder (13) (see FIG. 7B). The tips of the tissue graspers (12) may be disengaged from each other. More specifically, the two tissue graspers (12) forming a pair have the same length, and are accommodated to shift so that the tips are placed on one another.

In addition, the tissue joining device (11) includes a grip, a tissue-grasper accommodating cylinder trigger, a tissue grasper trigger, and the holder (6). The holder (6) includes the central conductor (7) and the external conductor (8).

When the user or the operator (doctor) holds the grip in the hand and moves (pulls) the tissue-grasper accommodating cylinder trigger in the proximal direction of the longitudinal axis (X) with the index finger, the tissue-grasper accommodating cylinder (13) is moved in the proximal direction of the longitudinal axis (X). Accordingly, the two tissue graspers (12) are released from the tissue-grasper accommodating cylinder (13).

In addition, conversely, the auxiliary tools (tissue graspers) may be pushed out from an inside of the external cylinder (tissue-grasper accommodating cylinder). More specifically, when the tissue grasper trigger is moved (pushed) in the distal direction of the longitudinal axis (X), the tissue graspers (12) move in the distal direction of the longitudinal axis (X), and are released from the tissue-grasper accommodating cylinder (13).

Then, when the tissue grasper trigger is moved (pulled) in the proximal direction of the longitudinal axis (X), the tissue graspers (12) move in the proximal direction of the longitudinal axis (X) to come closer with each another to hook the portions of the targeted attaching tissues (see FIG. 7A), and further, the portions of the targeted attaching tissues are brought into contact with each other or placed on one another (see FIG. 7B). Next, the portions having been brought into contact with each other or placed on one another are coagulated and/or fastened with use of microwaves to fix (join) the target tissues.

In addition, conversely, the auxiliary tools (tissue graspers) may be pulled in the external cylinder (tissue-grasper accommodating cylinder). More specifically, when the tissue-grasper accommodating cylinder trigger is moved (pushed) in the distal direction of the longitudinal axis (X), the tissue-grasper accommodating cylinder (13) moves in the distal direction of the longitudinal axis (X). The tissue graspers (12) come closer with each other to hook the portions of the targeted attaching tissues, and further, the portions of the targeted attaching tissues are brought into contact with each other or placed on one another (see FIG. 7B). Next, the portions having been brought into contact with each other or placed on one another are coagulated and/or fastened with use of microwaves to fix (join) the target tissues.

(Application of Tissue Joining Device Including a plurality of Tissue Graspers)

Unlike the related-art tissue joining device (see FIG. 1), in the state in which the plurality of tissue graspers (12) are accommodated in the tissue-grasper accommodating cylinder (13), the tissue joining device (11) including the plurality of tissue graspers of the present invention can be used in a thin tube and used for joining in the vertical direction. Therefore, the tissue joining device (11) can be preferably used in additional suturing and joining under open surgery, endoscopic surgery, endoscopic surgery, catheter surgery, and the like.

(Structure of Tissue Joining Device)

The tissue joining devices (1) and (11) of the present invention may be connected to a microwave generator through a microwave transmit section formed of a coaxial cable.

In the present invention, the central conductor (7) and the external conductor (8) are formed of so-called an electrical conductor. It is preferred that the conductor be made of a non-magnetic material. The non-magnetic material is, as a specific example, brass (copper+tin), phosphor bronze (copper+tin+phosphorus), copper, zinc, gold, silver alloy, or the like. An insulator is not particularly limited as long as a substance is used to have a heat resistance property with which electricity or heat is hardly transmitted. A heat resistance temperature is not particularly limited as long as the temperature is about 120° C. or higher.

The coaxial cable connecting an output source to the central conductor (7) serves as, in a case of a stationary oscillator, a microwave transmit section and can be a flexible and bendable cable having a tube shape (tube covering the coaxial cable). In a portable oscillator, the coaxial cable is an electrical cord.

In the tissue joining devices (1) and (11) of the present invention, microwaves are applied to joined target living tissues or the like by the central conductor (7) through the coaxial cable from the output source. In the present invention, a voltage to be applied is preferably from 1 V to 60 V. When the voltage is higher than 60 V, there is a risk in that damage on the tissues increases. Further, the voltage from 1 V to 15 V is in a condition in consideration of hemostasis of microvessels and avoidance of thermal damage in the vicinity (neuro-brain surgery).

EXAMPLE 1

(Confirmation of Effect of Prototype Device of Tissue Joining Device Including Protruding Section and Receiving Section)

A joining effect of the tissues was confirmed with use of a prototype device of the tissue joining device (1) including the protruding section (2) and the receiving section (3) of the present invention. Details are as follows.

(Prototype Device)

The prototype device is illustrated in FIGS. 4A and 4B. The protruding section (2) is connected to the central conductor (7) configured to apply microwaves, and the receiving section (3) is connected to the external conductor (8) configured to receive microwaves. The tip of the protruding section (2) is oriented in the proximal direction of the longitudinal axis (X) of the tissue joining device, the tip of the receiving section (3) is oriented in the distal direction of the longitudinal axis (X), and the tip of the protruding section (2) is located on a distal side with respect to the tip of the receiving section (3).

A diameter of the prototype device was about 7 mm, and the prototype device can be sufficiently used in an endoscopic port.

(Confirmation of Joining Effect)

Figure 8A:
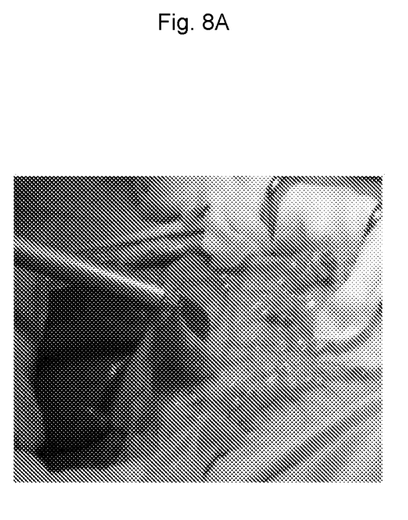
FIG. 8A is a photograph for showing a state of joining the target tissues (mesentery) with use of the prototype example of the tissue joining device including the protruding section and the receiving section.

A beagle dog was used for confirmation of a joining effect. Through laparotomy, a greater omentum (mesentery) was taken out of a wound. Next, the greater omentum (tissues) was sandwiched by the protruding section (2) and the receiving section (3) of the prototype device (FIGS. 4A and 4B). Then, microwaves (40 W) was applied (irradiated) to the sandwiched tissues for ten seconds to coagulate and fasten the sandwiched tissues so as to fix (join) the target tissues (see FIG. 8A).

Figure 8B:
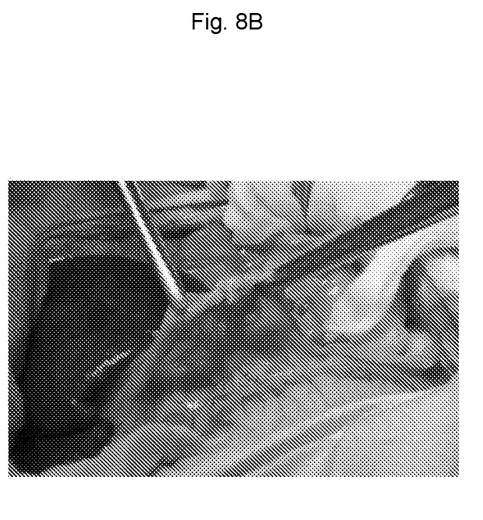
FIG. 8B is a photograph for showing a state of confirming fixation strength by pulling the joined portions.

Next, the joined portion was pulled to confirm the strength of the fixation, and it was confirmed that a joining effect was obtained which was equal to or more than that in the related-art suturing device (see FIG. 8B).

INDUSTRIAL APPLICABILITY

As described above, the tissue joining device of the present invention can achieve, in a surgical treatment area in a medical field, joining of living tissues by applying microwaves to the living tissues and the like which are joined target. Particularly, the tissue joining device can be used in a thin tube and can be used for joining in endoscopic surgery and the like. Therefore, the tissue joining device of the present invention is a surgical instrument which can join vertically, is easy to handle, and can easily join tissues. Further, the tissue joining device does not emit mist and smoke, is excellent to have extremely strong hemostatic ability, and, is also suitable as a surgical instrument in a limited space.

REFERENCE SIGNS LIST

1: tissue joining device including protruding section and receiving section
2: protruding section
3: receiving section
4: grip
5: trigger
6: holder
7: central conductor
8: external conductor
9: insulator
10: tissue
11: tissue joining device including a plurality of tissue graspers
12: a plurality of tissue graspers
13: tissue-grasper accommodating cylinder
X: longitudinal axis direction of tissue joining device, with arrow indicating distal direction of tissue joining device

The invention claimed is:

1. A tissue joining device, comprising: a protruding section directly or indirectly connected to a central conductor configured to apply microwaves, or the protruding section including the central conductor configured to apply microwaves; and a receiving section directly or indirectly connected to an external conductor configured to apply microwaves, or the receiving section including the external conductor configured to apply microwaves, wherein each of the receiving section and the protruding section are conductive so as to at least apply microwaves or receive microwaves, wherein the receiving section includes a tip oriented in the distal direction of the longitudinal axis, the protruding section includes a tip and a U-shaped bend such that the tip of the protruding section is oriented in the proximal direction of the longitudinal axis, and the receiving section, the tip of the receiving section, and the tip of the protruding section are disposed along a common axis, and the tip of the receiving section is located on a proximal side with respect to the tip of the protruding section on the longitudinal axis, and the tip of the protruding section is configured to move in the proximal direction of the longitudinal axis, and wherein, through the movement of the tip of the protruding section, portions of targeted attaching tissues are brought into contact with each other or placed on one another by the protruding section and the receiving section, the protruding section and the receiving section are configured to apply microwaves to the portions from the central conductor and the external conductor, respectively, and further, the portions having been brought into contact with each other or placed on one another are coagulated and/or fastened by the microwaves to fix the target tissues.

2. The tissue joining device according to claim 1, wherein the tissue joining device is to be used for surgery with a narrow view.

3. The tissue joining device according to claim 1, wherein the tissue joining device is to be used for endoscopic surgery.

4. The tissue joining device according to claim 1, wherein the tip of the protruding section tapers to a point, and the tip of the receiving section comprises a planar surface perpendicular to the longitudinal axis.

5. A tissue joining device, comprising: a protruding section directly or indirectly connected to a central conductor configured to apply microwaves, or the protruding section including the central conductor configured to apply microwaves; and a receiving section directly or indirectly connected to an external conductor configured to apply microwaves, or the receiving section including the external conductor configured to apply microwaves, wherein each of the receiving section and the protruding section are conductive so as to at least apply microwaves or receive microwaves, wherein the receiving section includes a tip oriented in a distal direction of the longitudinal axis, the protruding section includes a tip and a U-shaped bend such that the tip of the protruding section is oriented in a proximal direction of the longitudinal axis, and the receiving section, the tip of the receiving section, and the tip of the protruding section are disposed along a common axis, and the tip of the receiving section is located on a proximal side with respect to the tip of the protruding section on the longitudinal axis, wherein portions of targeted attaching tissues are brought into contact with each other or placed on one another by the protruding section and the receiving section when the tip of the protruding section moves in the proximal direction of the longitudinal axis, the protruding section and the receiving section are configured to apply microwaves to the portions from the central conductor and the external conductor, respectively, further, the portions having been brought into contact with each other or placed on one another are coagulated and/or fastened by the microwaves to fix the target tissues, wherein the tissue joining device comprises a trigger configured to move the tip of the protruding section in the proximal direction of the longitudinal axis, and wherein the tip of the protruding section is moved in the proximal direction of the longitudinal axis when the trigger is moved in the proximal direction of the longitudinal axis, and the portions of the targeted attaching tissues are brought into contact with each other or placed on one another by the protruding section and the receiving section.

6. The tissue joining device according to claim 5, wherein the tip of the protruding section tapers to a point, and the tip of the receiving section comprises a planar surface perpendicular to the longitudinal axis.

* * * * *